(12) United States Patent
Dogariu

(10) Patent No.: US 6,738,144 B1
(45) Date of Patent: *May 18, 2004

(54) NON-INVASIVE METHOD AND LOW-COHERENCE APPARATUS SYSTEM ANALYSIS AND PROCESS CONTROL

(75) Inventor: Aristide Dogariu, Oviedo, FL (US)

(73) Assignee: University of Central Florida, Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,586

(22) Filed: Dec. 17, 1999

(51) Int. Cl.⁷ ................................................ G01B 9/02
(52) U.S. Cl. ..................... 356/479; 356/335; 356/497
(58) Field of Search ............................... 356/479, 477, 356/335, 450; 250/227.19, 222.27

(56) References Cited

U.S. PATENT DOCUMENTS

| | | | |
|---|---|---|---|
| 4,595,291 A | 6/1986 | Tatsuno | 356/336 |
| 4,928,007 A | 5/1990 | Fürstenau et al. | 341/137 |
| 5,202,745 A | 4/1993 | Sorin et al. | 356/73.1 |
| 5,218,418 A | 6/1993 | Layton | 356/345 |
| 5,218,419 A | 6/1993 | Lipson et al. | 356/345 |
| 5,268,738 A | 12/1993 | Baney et al. | 356/345 |
| 5,365,335 A | 11/1994 | Sorin | 356/345 |
| 5,491,552 A | 2/1996 | Knüttel | 356/360 |
| 5,517,303 A | 5/1996 | Cole et al. | 356/345 |
| 5,557,400 A | 9/1996 | Sorin et al. | 356/73.1 |
| 5,798,834 A | 8/1998 | Brooker | 356/345 |
| 5,815,264 A | 9/1998 | Reed et al. | 356/336 |
| 5,847,827 A | 12/1998 | Fercher | 356/345 |
| 5,867,268 A | 2/1999 | Gelikonov et al. | 356/345 |
| 5,892,583 A | 4/1999 | Li | 356/345 |
| 6,011,626 A * | 1/2000 | Hielscher et al. | 356/367 |
| 6,256,102 B1 * | 7/2001 | Dogariu | 356/479 |

OTHER PUBLICATIONS

Optical Path–Length Spectroscopy of Wave Propagation in Random Media, G. Popescu and A. Dogariu, Optics *Letters*, vol. 24, No.7, Apr. 1, 1999, pp. 442–444.

* cited by examiner

Primary Examiner—Frank G. Font
Assistant Examiner—Phil Natividad
(74) Attorney, Agent, or Firm—Law Offices of Brian S. Steinberger, P. A.; Brian S. Steinberger (57) ABSTRACT

The disclosure relates to measuring devices that are particularly suited for the purpose of in-situ characterization of particles present in fluid substances or in air using a low-coherence interferometer. Specifically, the characterization includes average size, size distribution, volumetric density, and composition. The low-coherence interferometer utilizes a split band of radiation to illuminate a sample probe and a reference probe then combines the reflected radiation from both probes to determine the photon pathlength distribution of the tested particulate or colloidal containing stream and from this information determine the size characteristics of said stream. The methodology is relevant to possible spatially distributed control of chemical processes such as emulsion polymerization to produce paints, coatings, synthetic rubbers, or crystallization processes in pharmaceuticals, food, and bulk chemicals industries. Another application relates to on-line control of particle size and volumetric density is in combustion for diagnostics. The invention can be used for the characterization of coal particles, dense sprays and solid propellants or any other system, which is too dense for conventional optical measurement techniques. Beside the intrinsic particulate nature of these systems, random index of refraction variations are also created due to turbulence/temperature interactions. The remote optical characterization of systems with high-concentration of suspended solids is also important for water quality control and pollution monitoring.

20 Claims, 6 Drawing Sheets

NON-INVASIVE METHOD AND LOW-COHERENCE APPARATUS SYSTEM ANALYSIS AND PROCESS CONTROL

This invention relates to the optical characterization of particulate dispersions, and in particular to a method and apparatus for the in-situ physical analysis of particles present in fluid substances or in air.

BACKGROUND AND PRIOR ART

There are many applications where particle characterization measurements can provide for improved process control leading to increased throughput, higher recovery rates, reduced reagent consumption and better product quality. These benefits result in reduced cost and increased profits, strong justifications for the use of process control instrumentation. Unfortunately, there is a lack of particle measurement instrumentation that can be used in-situ for real time measurements that are necessary for process control. In a typical process, such as a polymerization or crystallization reaction, particles or droplets are suspended in a flowing medium, liquid or gaseous, while chemical or physical changes are taking place to the materials in the slurry. In many cases these changes are very dynamic, and thus the materials cannot be measured when removed from the pipeline or vessel requiring the instrumentation to be non-invasive.

Of the common approaches to particle size determination, light scattering is one of the most attractive alternatives, which, besides its intrinsic non-invasive and nonpertubative character, has also the potential for developing high performance online instrumentation and sensing procedures. Current optical technologies utilizing light scattering for particulate characterization are based on: turbidity (see U.S. Pat. No. 4,537,507); dynamic light scattering (see U.S. Pat. Nos. 5,155,549 and 5,502,561); or angular resolved light scattering (see U.S. Pat. No. 5,438,408). These methods require substantial sampling and dilution procedures and therefore are not very suitable for on-line process monitoring. Besides, these approaches are intrinsically invasive.

Advances have been made to develop on-line characterization technologies. Optical techniques are usually preferred because they can be non-invasive, inexpensive and reliable. Several techniques that are pertinent to on-line determination of various properties of particles present in fluid substances have been proposed and are based on: diffusive wave spectroscopy (see U.S. Pat. Nos. 5,365,326 and 5,818,583); coherent backscattering (see U.S. Pat. No. 5,063,301); photon density modulation (see U.S. Pat. No. 4,890,920); and, time-resolved measurements (see U.S. Pat. No. 5,740,291). Thus, the non-invasive optical methods have many advantages for particle sizing, but also have one serious limitation. At high particle concentrations, light is scattered from particle to particle, and such so-called multiple scattering results in loss of precision in the optical measurements.

When light strikes the boundary surface separating two media of different optical densities, some of the incident energy is reflected back. This property is referred to as reflectance and by some authors as backscattering from the interface. The techniques used to measure this property fall under the broad definition of reflectometry. This is different from the backscattering of light that undergoes multiple scattering trajectories in particulate media. It is important to realize this distinction between the single backscattering (reflection) of light from an interface and the light backscattered from a system of particles due to a multiple scattering process. Well known instruments that detect the position and strength of one inhomogenity, i.e., single-scattering in the back scattering direction, are those that rely on low-coherence optical interferometry (sometimes called white light interferometry).

The deficiencies in the current optical light scattering approach are due to the fact that they are based on single interactions between interrogating light wave and specific particles. Therefore, the current methods cannot account for multiple scattering effects and are not appropriate for measurements at high volume fractions of particles such as powders. Many of the current techniques are also limited because of the need for sample preparation and because of their typical bistatic (different locations for source and detector) geometry.

SUMMARY OF THE INVENTION

The first objective of the present invention is to provide an optical apparatus for system analysis and process control.

The second objective of this invention is to provide a non-invasive means for optical characterization of particulate fluids.

The third objective of this invention is to provide a low-coherence interferometer for determining the optical path length distribution for light reflected from a random medium.

The fourth objective is of this invention is to provide a low-coherence interferometer with multiple measuring heads.

The fifth objective of this invention is to provide a low-coherence interferometer with an optical switch between different measuring heads.

The sixth objective of the invention is to provide a low-coherence interferometer with multiple wavelength sources.

The seventh objective of the invention is to provide a complex system where low-coherence interferometry LCI information can be enhanced and complemented by the use of time-resolved data. In the same basic configuration, the light source(s) can be modulated at high frequencies and phase and/or amplitude of the LCI signal can be monitored. This information will complement the steady state measurement and will offer the possibility to discriminate between absorption at the particle level.

The primary embodiment of the invention provides a low-coherence interferometer apparatus for determining the size characterization of a stream of particulate or colloidal suspension by means of a split beam of electromagnetic radiation illuminating both a sample probe positioned in said stream and a reference probe, the beam reflections of both probes are combined to provide an interference signal and this signal is thereafter analyzed to provide a photon pathlength distribution whereby the size characterization of said stream is determined. The method of the invention includes the steps of illuminating both an in-situ sample of a steam of particulate or colloidal substances and a reference with a common level of low-coherent electromagnetic radiation and thereafter combining the resultant reflected radiation from said sample and said reference to provide an interference signal whereby the photon pathlength distribution of said sample is realized and thus providing indicia determinative of the size characterization of said stream.

Further objectives and advantages of this invention will be apparent from the following detailed description of a

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

The invention uses low-coherence interferometry (LCI) in the regime of multiple scattering to noninvasively characterize processes that involve particulate matter. The LCI technology was developed to measure reflectivity's of dielectric interfaces and also to suppress multiple scattering noise in imaging applications such as low-coherence tomography.

The present invention uses the LCI information, i.e., the photon pathlength distribution (PPLD), to determine the characteristics of a sample from a process by comparing the PPLD to that expected or to that of known samples. This information can be further use to control the process in real time.

Photon pathlength distribution (PPLD) can also be used to obtain a sample-specific optical property (the transport mean free path, hereinafter noted as l*) that can be further used to assess the structural information of interest: particle size, volume fraction, and porosity, phase transitions, and the like, which affect the inhomogeneous distribution of the refractive index.

Alternatively, PPLD can be used to obtain the sample-specific optical property called the transport mean free path l*. Commonly the light propagation through inhomogeneous and multiple scattering media can be described in terms of a radiative transport theory. Within the frame of this theory, a photon diffusion approximation (PDA) establishes a direct relationship between averaged measurable properties such as diffuse reflection or transmitance and microstructure characteristics of the scattering medium. The l* parameter is this medium-specific parameter that describes the microstructure (particle size, number density, etc.) and can be, therefore, inferred from measurements. When interpreted in the PDA frame, PPLD depends only on a single parameter, l*, that is sample-specific. Accordingly, besides a direct comparison with expected or know shapes, PPLD can be fitted with a PDA model to obtain a specific parameter that can be used to classify the medium or can be followed during specific technological processes. The values of this parameter can be also further used to assess the structural info of interest.

The invention can be fiber-optics-based. Accordingly, a distributed process control can be realized where a single light source and processing unit is used and several measurement points are interrogated simultaneous or successively. Moreover, the fiber-optics-based allows remote control of industrial processes.

The use of different measuring head geometry (point-like source or plane-wave source, for instance) permits one to directly discriminate the single-scattering effects and, therefore, to measure particle size independent of particle number density. The extremely high dynamic range of the LCI method allows covering a broad range of particulate concentrations practically from single-scattering regime to dense media with essentially multiple scattering characteristics.

The use of two or more light sources, or a tunable light source, provides additional characterization ability. Use of two different wavelengths permits one to make concentration-independent particle size measurement and the use of multiple wavelengths allows one to determine the particle size distribution and element composition from the absorption spectra. Implementation of multi-wavelength instrumentation can be done based on fiber optics switches and couplers.

Another objective of this invention is to provide a complex system where the LCI information can be enhanced and complemented by the use of time-resolved data. In the same basic configuration, the light source(s) can be modulated at high frequencies and phase and/or amplitude of the LCI signal can be monitored. This information will complement the steady state measurement and offer the possibility to discriminate between absorption at the particle level.

The subject invention can use components of prior art low-coherence interferometers. See U.S. Pat. No. 5,202,745 to Sorin; U.S. Pat. No. 5,323,229 to May; U.S. Pat. No. 5,365,335 to Sorin; U.S. Pat. No. 5,646,724 to Venkatesh; and U.S. Pat. No. 5,847,827 to Fercher, all of which are incorporated by reference.

The resemblance with previous art, i.e., the use of low-coherence (white-light) interferometry, is that those devices convert changes in the light intensity into an electrical signal. This conversion is done through a heterodyne scheme where the light intensity containing the information is combined with a reference light intensity. From the prior art, the following components can be used: schemes for noise reduction in low-coherence relectometry; schemes for improved detection in low-coherence relectometry; and schemes to measure polarization independent signals.

Figure 1:
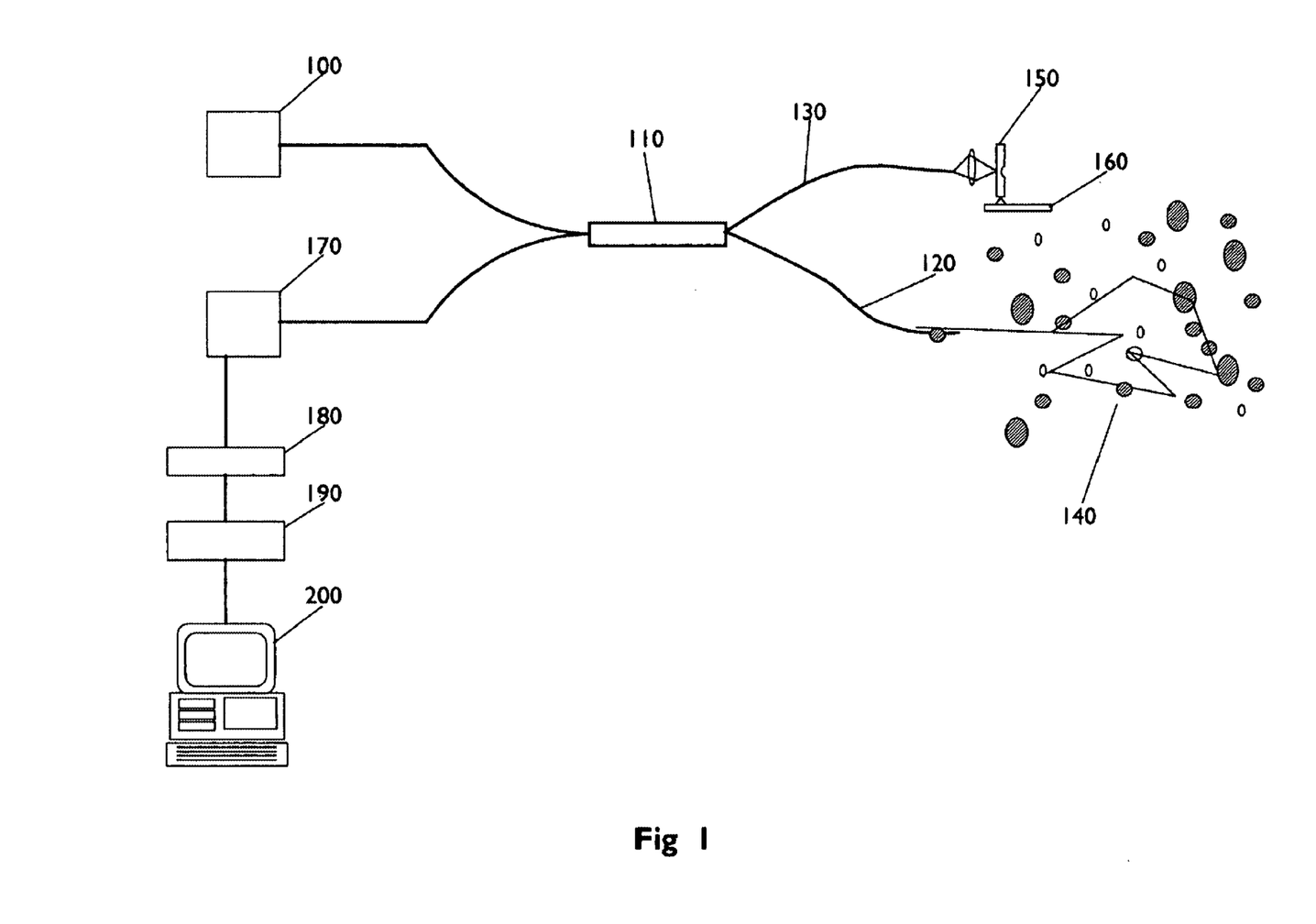
FIG. 1 is a schematic setup of a first embodiment of the low-coherence apparatus invention.

Referring to FIG. 1, the broad bandwidth light source 100 can be Hamamatsu model #L3302 having a wavelength of approximately 830 nm. Splitter 110 can be a Newport beam splitter. Probe 120 can be a single mode optical fiber. Reference 130 light beams can have a frequency of 1 KHz. Sample 140 can be a polstyrene bead stream. Reference mirror 150 can be a 1 cm diameter mirror. Power detector 170 can be a NewFocus Nirvana detector. Frequency filter 180 can be a Stanford Research SR650 filter. Signal analyzer 190 can be a SR 760 analyzer, and the computer 200 can be an IBM 486.

As shown in FIG. 1, light from a broad bandwidth light source 100 is first split 110 into probe 120 and reference 130 light beams which are both retroflected, from a target region of the sample 140 and from a reference mirror 150, respectively, and are subsequently recombined to generate an interference signal.

In low-coherence interferometry, light from a broad bandwidth source is first split into probe and reference beams which are both retroreflected from a targeted scattering medium and from a reference mirror, respectively, and are subsequently recombined to generated an interference signal. When two stationary optical field $U_1$ and $U_2$ are physically overlapped, the expression for the resultant intensity is written as:

$$I = I_1 + I_2 + 2Re[\Gamma_{12}(\tau)], \quad (0.1)$$

Where $$I_k = <U_k(t) \cdot U_k^*(t)>, k=1,2 \quad (0.2)$$

represents the average intensity associated to the field $U_k$ and $$\Gamma_{12}(\tau) = <U_1(t+\tau) \cdot U_2^*(t)> \quad (0.3)$$

is the mutual coherence function of the two filed which depends on $$\tau = t_2 - t_1,$$

the propagation time difference corresponding to the two waves. The angular brackets denote the average taken over the ensemble of possible realizations and usual notations are used for the real part and the conjugate of a complex number. Introducing the complex degree of coherence:

$$\gamma_{12} = \frac{\Gamma_{12}(\tau)}{\sqrt{I_1} \cdot \sqrt{I_2}}, \quad (0.4)$$

The resultant intensity becomes:

$$I = I_1 + I_2 + 2 \cdot \sqrt{I_1} \cdot \sqrt{I_2} Re[\gamma_{12}(\tau)]. \quad (0.5)$$

This represents the general interference law for stationary optical fields and it shows that the intensity resulted from the superposition of two beams depends on the individual intensities and also on the real part of the complex degree of coherence. Let us consider now the classical Michelson interferometer with a fixed reference mirror in one arm and a random medium replacing the mirror in the other arm. Assuming quasi-monochrmatic optical fields ($\Delta\lambda/\lambda << 1$), the detected intensity is obtained in a simple form:

$$I_d = I_s + I_{ref} + 2 \cdot \sqrt{I_s} \cdot \sqrt{I_{ref}} \cos(2\pi \cdot \Delta s/\lambda) \quad (0.6)$$

where $I_d$, $I_s$, and $I_{ref}$ are the detected, scattered, and reference intensity, respectively.

In the last equation, the optical path difference between the scattered and reference field is $$|\Delta s| < l_{coh},$$

denoted by $\Delta s$ and $\lambda$ is the central wavelength. It follows that two conditions are needed in order to obtain fringes of interference: i) $\Delta s$ to be a multiple of wavelength and ii), where $l_{coh}$ is the coherence length of the source.

Constructive interference between the probe and reference beams occurs only if the optical path difference between them is less than the coherence length of the source.

Sweeping the reference arm 160 and synchronously recording the interference signal one measures optical signatures corresponding to predetermined depths in the sample.

The interference signal is first detected by a power detector 170, the electrical signal is frequency filtered 180 and then amplified by an amplifier 190. The digitized signal is further processed by computer 200 using commercial data processing software such as Labview (produced by National Instruments Co.)

Figure 2:
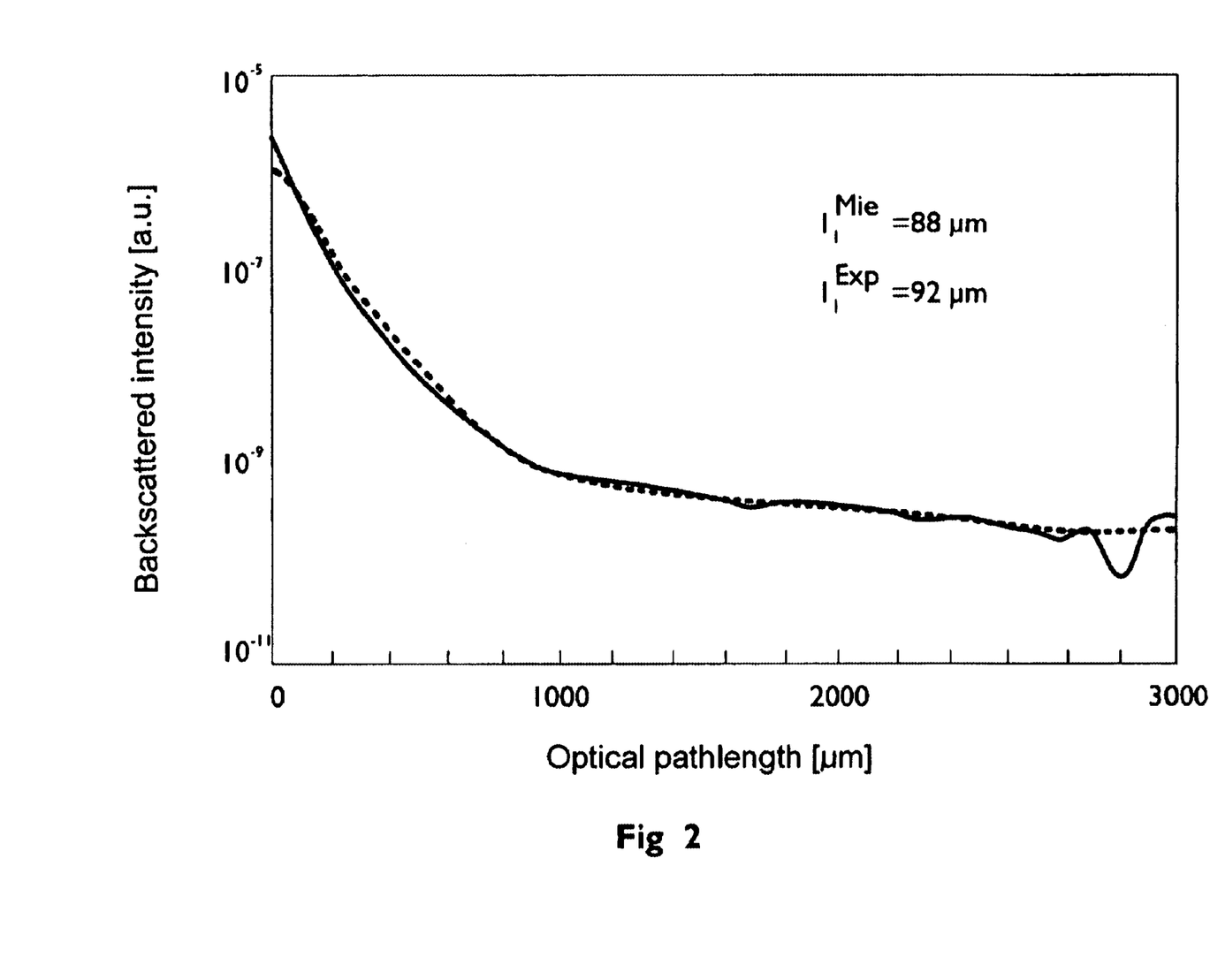
FIG. 2 shows a plot of the photon pathlength distribution realized with the embodiment of FIG. 1.

The strength of the interference signal depends on the amount of light collected in the probe arm and, therefore, it maps the reflectivity of the sample as scanned by the probe beam with typical data shown in FIG. 2.

$$|\Delta s| < l_{coh},$$

The subject invention relates to the analysis of particulate matter with multiply scattered light. Photon pathlength distribution (PPLD) can be recorded directly when the targeted region 140 consists of random distributions of particulates, inhomogeneities or, more generally, any kind of random distribution of refractive index variations. Typical PPLD is shown in FIG. 2 and consists of backscattered intensity contributions corresponding to waves scattered along closed loops that have the same optical pathlengths. The data correspond to backscattering collected at 1300 nm from a dense colloidal dispersion of polystyrene microspheres. Analysis of signal lineshape can be performed in the frame of a general photon diffusion theory where the fitting parameters of the curve are the photon mean free path l* and the averaged backscattering cross-section of the particles in suspension.

The particular configuration of low-coherence interferometry is such that the source and the detector are physically overlapped. The incident beam is considered to be narrow, collimated and normal to the surface of the smi-infinte homogeneous medium. The source is stationary, but, as we discussed previously, the information about optical pathlength distribution can be obtained by applying a time-dependent diffusion approach. Although the light propagation through the random medium far from the source is completely diffusive and propagation at distances longer than l* should obey diffusion equation, on should not expect for time-dependent diffusion equation to give good results close to the boundary or, correspondingly, at short optical pathlengths. In this region the backscattering arising from single scattering events (ballistic component) becomes dominant. In media with negligible absorption, the diffuse density $$\Psi(r, t)$$

satisfies the equation:

$$\frac{\partial \Psi(r, t)}{\partial t} = D\nabla^2 \Psi(r, t) + \delta(r)\delta(t) \quad (0.7)$$

where $$\delta(r)\delta(t)$$

is the impulse source at time t=0 and r=0 and D is the diffusion coefficient given by $$D = (v \cdot l_t)/3.$$

Setting the boundary condition such that the photon density vanishes on a plane situated at a distance z0 from the interface the temporal dependence of the energy density at a distance r from the source is given by:

$$\Psi(r, t) = S_0(4\pi Dt)^{-3/2} \cdot \left[1 - \exp\left(-\frac{z_0^2}{4Dt}\right)\right] \cdot \exp\left(-\frac{r^2}{4Dt}\right) \qquad (0.8)$$

where $$z_0 \cong 0.71 \cdot l^*.$$

The energy flux is obtained from Fick's law and is given by:

$$J(r, t) = S_0(4\pi Dt)^{-3/2} \cdot \frac{z_0}{t} \cdot \exp\left(-\frac{r^2 + z_0^2}{4Dt}\right) \qquad (0.9)$$

Assuming an average transport velocity v for photons traveling within the medium, a simple proportionality relationship can be established between time and optical pathlength s=vt. The particular LCI geometry is obtained by setting r=0 and the corresponding expression for the diffusion component of the detected flux as a function of optical pathlength becomes:

$$J_d(s) = S_0(4\pi l^*/3)^{-3/2} \cdot z_0 v \cdot s^{-5/2} \exp\left[-\frac{z_0^2}{s(4l*/3)}\right] \qquad (0.10)$$

Characteristic for this equation is the $$s^{-5/2}$$

decay at large optical pathlengths. The use of diffusion equation to interpret the light propagation in random media (Eqs. 0.7 through 0.10) is well known.

The information contained in PPLD is similar to those obtained in time-resolved reflectance measurements where the diffusion approximation makes a reasonable description of the experimental data. In the dynamic experiments, by choosing an appropriate geometry such as large detector-source separations or integrating the reflectance over a large area, one can select mostly diffusive scattering contributions. In the backscattering configuration associated with the LCI in FIG. 1, on the other hand, the detector measures a diffusive component but it also allows the ballistically backscattered component to be collected. When the short optical pathlengths component becomes important in the total intensity balance, the LCI data offer one to independently estimate the backscattering cross-section. A phenomenological model is developed and can accurately account for both diffuse and ballistic component of the backscattered light and can be used to retrieve single scattering information in the presence of strong multiple scattering.

Figure 3:
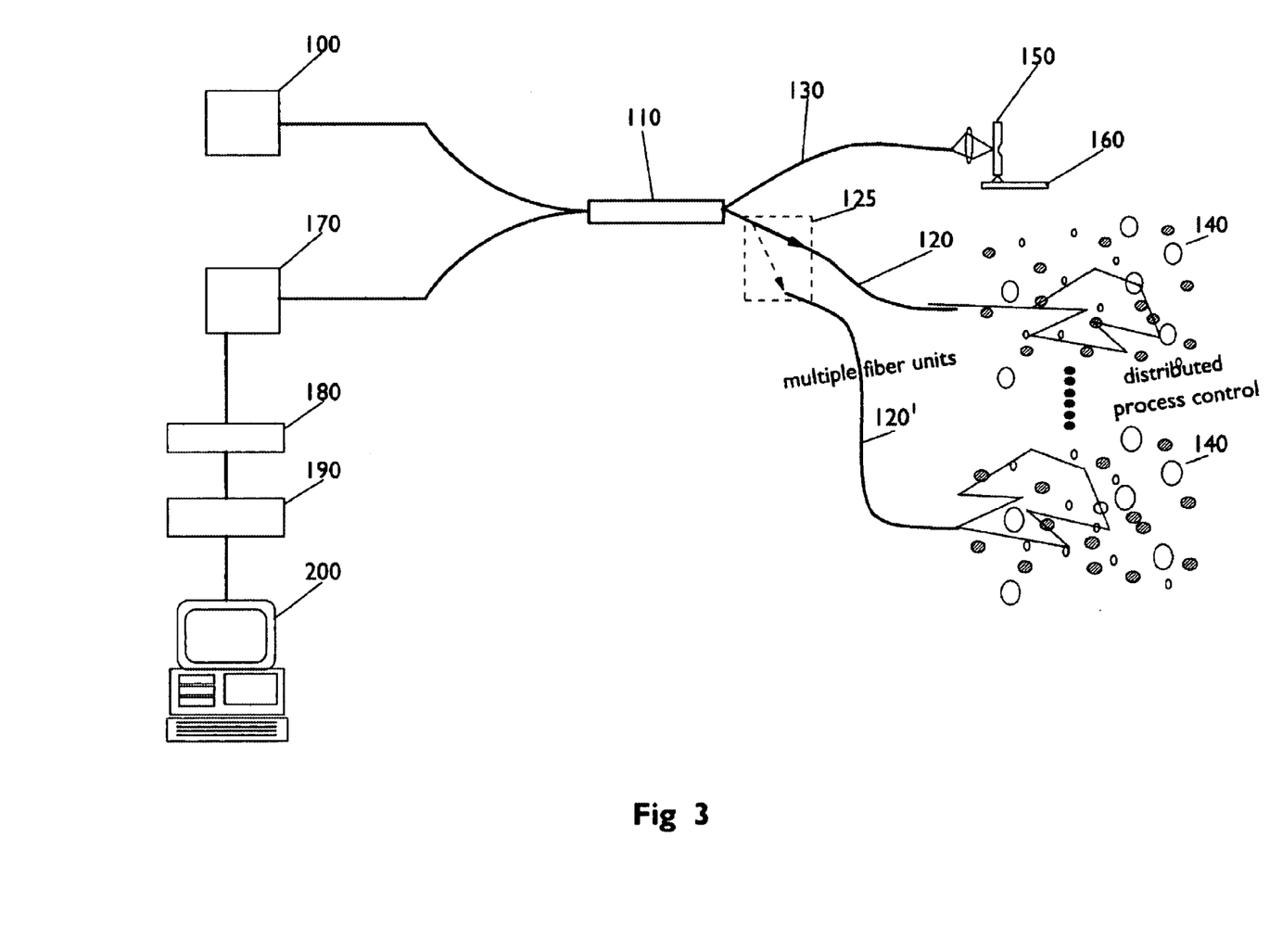
FIG. 3 is a schematic setup of the invention wherein the distributed process control is implemented by sequential measurement.

FIG. 3 is a schematic setup of the invention wherein the distributed process control is implemented by sequential measurement. A fiber multi/demultiplexer 125 (such as AWG0816SPM-SCSMF manufactured by NTT, splits and combines optical signals corresponding to different fiber optic measuring units 120 and 120'. Depending on the external electrical control of the switch 125, a specific measurement unit, such as fiber optic type, is selected. The location of these measurement units can be remotely distributed along the technological process the only constraint is that the length of the arms 130 and 120 are to be equal. The distance is practically limited by the optical attenuation along the fibers 120 and 130 but it can easily be extended to hundreds of meters. Typical data in FIG. 2.

Figure 4:
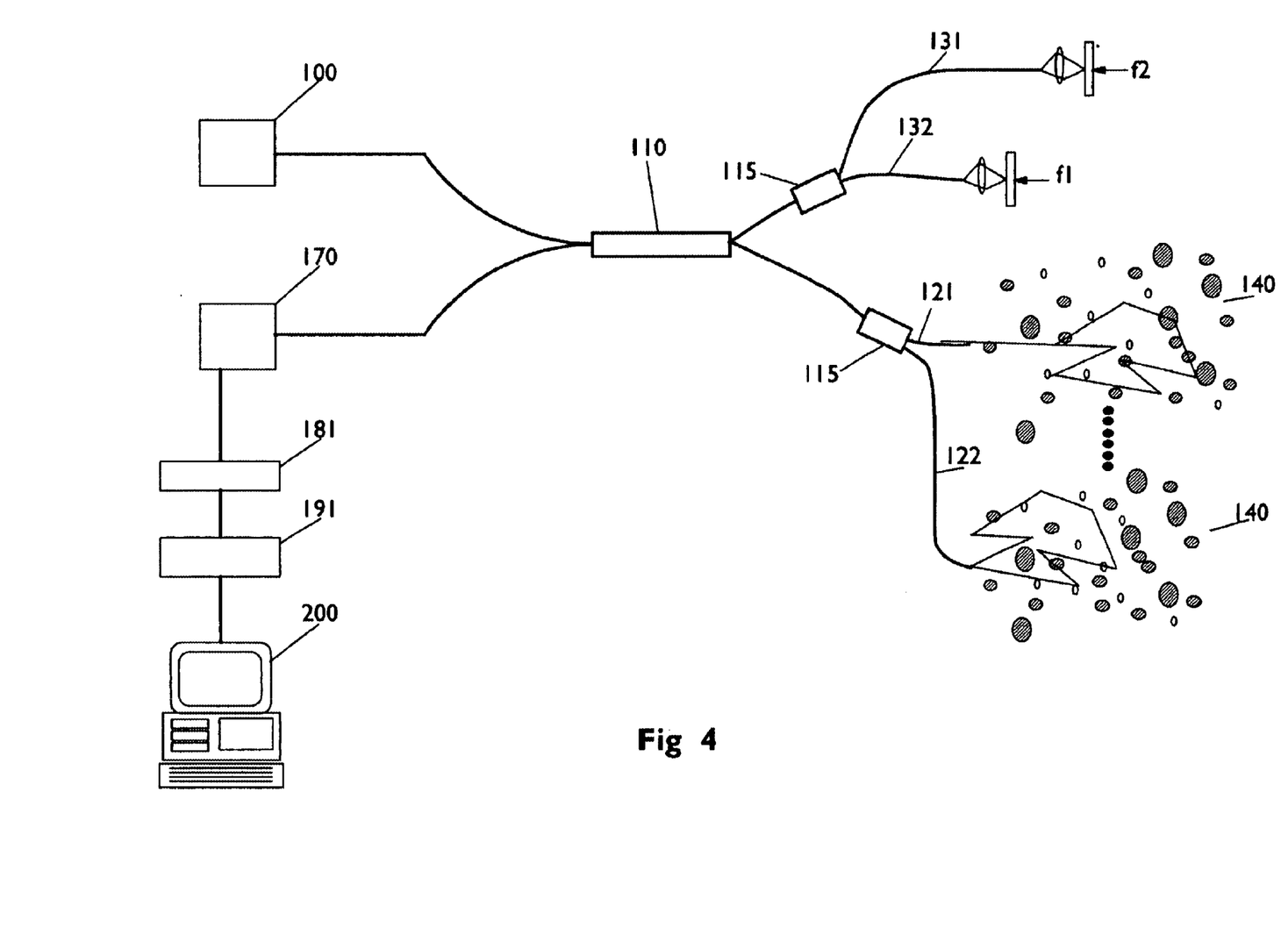
FIG. 4 is a schematic setup of the invention wherein simultaneous measurements can be performed at different locations.

In yet another configuration, simultaneous measurements can be performed at different locations. FIG. 4 is a schematic setup of the invention wherein simultaneous measurements can be performed at different locations. As shown in FIG. 4, two reference arms 131 and 132 can use different reference modulation frequencies f1 and f2 where f1 can be approximately 1 KHz and f2 can be approximately 5 KHz, which permit separate simultaneous measurements in the arms 121 and 122. The lengths of the arms are correspondingly matched 121 with 131 and 122 with 132. The only restriction is that the difference between these pairs be larger than the coherence length of the source (which typically is of the order of 10 microns). Although FIG. 4 shows only two measuring locations, their number is by no means limited as long as sufficient power is delivered by the source 100. Multiple filter 181 can be a SR 650 filter, narrow band amplifiers 191 can be a SR 760, and fiber optic splitters 115 can be a 1×2 Newport splitter.

Multiple filter 181 selects the frequencies f1 and f2 and different narrow-band amplifiers 191 are used to provide the signals for further processing in the computer unit 200. Fiber optic splitters 115 are used to distribute the light in different arms 121, 122.

The analysis in computer 200 comprises the same steps as before to obtain PPLD corresponding to measurements with different arms 121 and 122. The analysis can provide simultaneous PPLD's or l* data at two or more locations in the same sample or at various locations.

Figure 5:
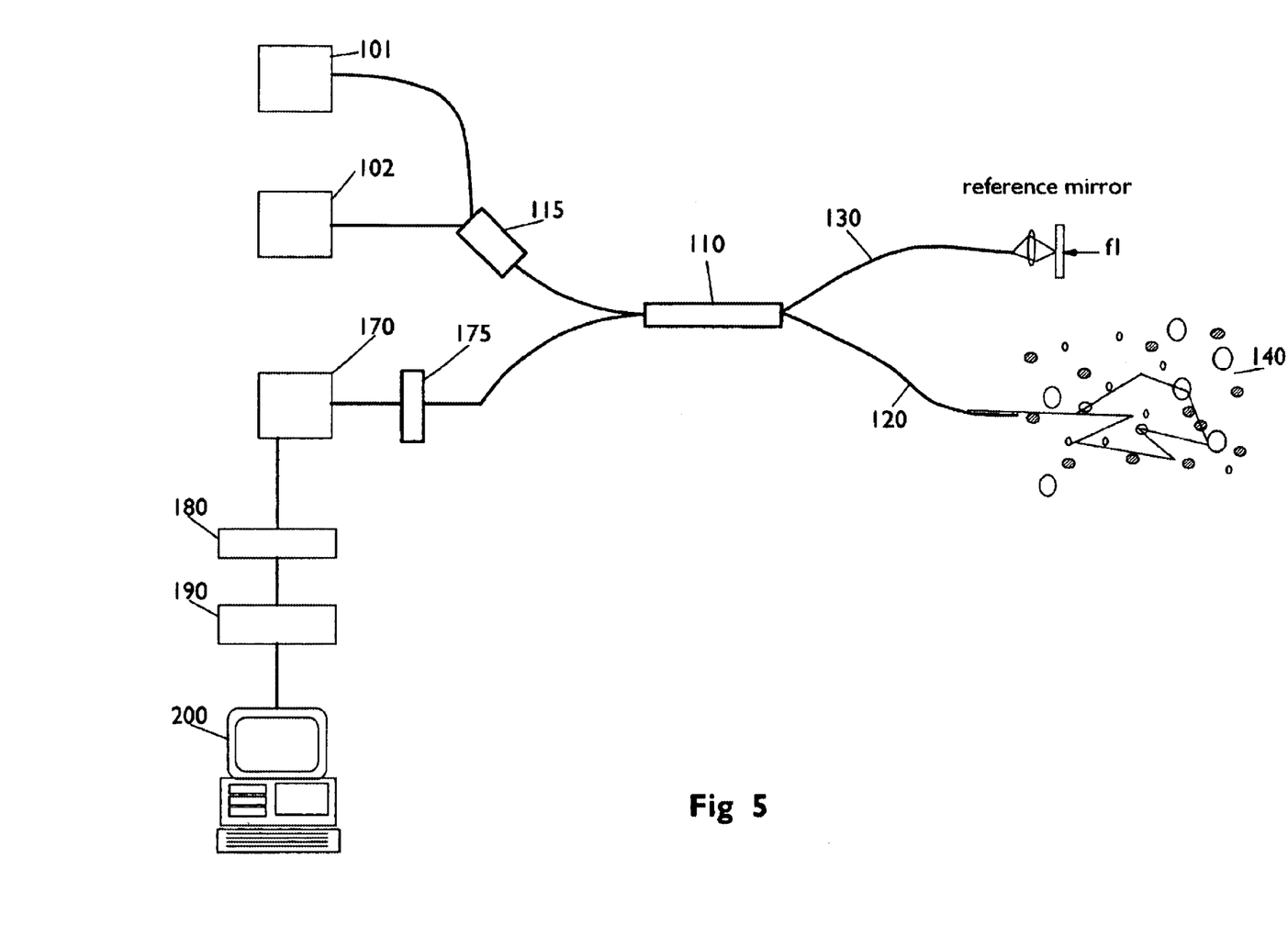
FIG. 5 is a schematic setup of a multi-wavelength apparatus of the invention.

FIG. 5 is a schematic setup of a multi-wavelength apparatus of the invention. Low-coherence sources with different central wavelengths denoted by 101, 102, and the like are coupled through a 1×2 fiber splitters 115. The ensemble of different sources can be replaced by a tunable source or by a very broad band source followed by a band-pass filter. A tunable filter 115 is introduced in front of the detector 170 to record signals at selected wavelengths. The signal-processing unit 200 will record PPLD corresponding to different wavelengths and obtain values of the scattering and absorption coefficients of the particles at these different wavelengths. Conventional algorithms are subsequently used to inversely solve for the size distribution of particles in the investigated sample.

Specific analysis can also be applied to obtain the concentration or number density of scattering particles in the targeted region. The analysis should be based on measured PPLDs and subsequent fitting with the dependence indicated in Eq. (0.10) The fitting parameter is l* which, in turn is given by $$\rho = [\rho^{-1}(\mu_a + \mu_s)]$$ where $\mu_a$ and $\mu_s$ are, Respectively, the absorption and scattering coefficients associated with the system of particles under test and p is the number density of particles.

When operated at various wavelengths $$\lambda,$$

the apparatus will record difference PPLDs similar to that presented in FIG. 2 but with different shapes due to the specific wavelength dependence of the scattering and absorption coefficients. Subsequent fitting procedures applied to these PPLDs will infer values of the scattering and absorption coefficients at the specified wavelengths.

Figure 6:
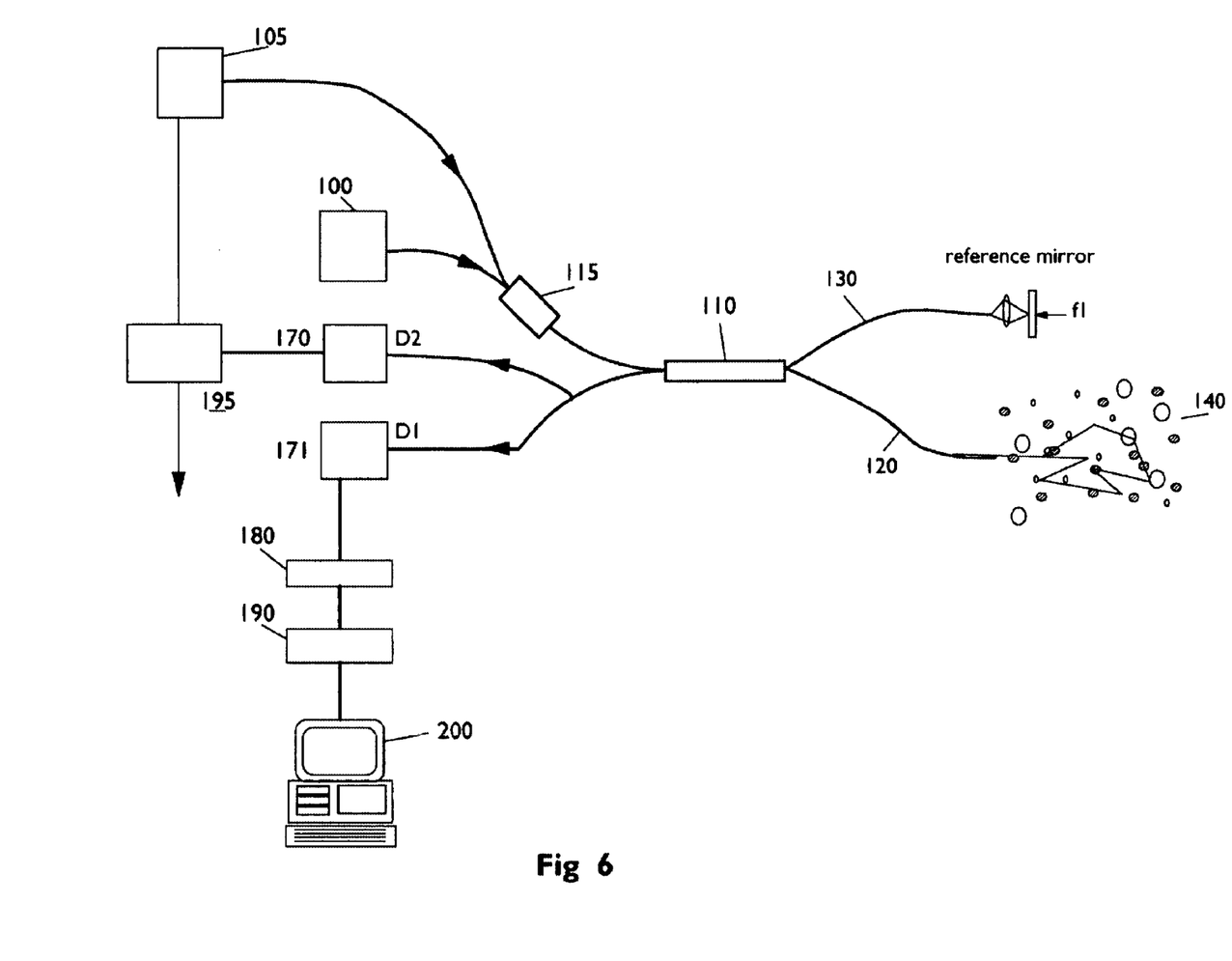
FIG. 6 is a schematic setup of the invention with a double path through a system containing a particulate suspension.

FIG. 6 is a schematic setup of the invention with a double path through a system containing a particulate suspension: a continuous illumination produced by the low-coherent source 100 and a pulsed illumination produced by the second light source 105. The time varying source 105 can be PDL-800 picosecond diode laser, discriminator 195 can be Time Harp 100 from Pico Quant GMBH, the supeluminiscent diode 100 can be a SLD produced by Superlum Inc. Component 170 refers to fast photodetector such as 102x from New Focus, and 171 refers to a photodetector Nirvana from NewFocus. The steady-state information contained in LLPD is recorded and analyzed as described before. In addition, the time-resolved information can be recorded by the detector D2, passed through the discriminator 195 and the time-dependent fluctuations can be future analyzed. A dependence similar to the one in Eq. 10 where the spatial variable s is replaced by a time variable t is obtained and can be used to extract the information about ^*. A similar fitting procedure as described above can be used to provide alternative values of the scattering and absorption coefficients which characterize the sample under test.

The apparatus and process described in the subject invention herein has wide application throughout industry including systems which require particle sizing in dense colloidal suspensions in adverse environments for it provides a backscattering configuration suitable for remote operations (such as turbulence, excessive temperature gradients and explosive conditions) and for particle sizing of powders (such as chemical, pharmaceutical, utilities, petrochemical cement and food industries). The invention described herein: performs equally well for liquid and suspended particle systems; is insensitive to total number of particles present in the scattering volume; offers instantaneous size formation averaged over a very large number of particles; does not require"two-side-open"transmission geometry; does not require absolute intensity measurements; uses "monostatic" geometry where the illumination and detection systems share the same optical axis; useful where the particle size is 3 microns and larger; is well suited for applications where the particles are non-spherical; and, applies equally well to stationary and dynamic systems.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A low-coherence interferometer apparatus useful for determining the size of particles of a known concentration in a stream of colloidal or particulate suspension comprising:
    at least one low-coherence light source;
    a split beam of electromagnetic radiation illuminating a sample probe positioned in the stream and a reference probe;
    means for combining the reflected illuminations from the sample probe and the reference probe to provide an interference signal;
    detector means for reading photon pathlength distribution of said interference signal; and
    means for obtaining the particulate size from the detector means.

2. The apparatus of claim 1 wherein the radiation is provided by:
    a plurality of low-coherence sources each having different central wavelengths; and
    a plurality of said sample probes and a tunable filter positioned prior to said sample probes.

3. The apparatus of claim 1 wherein the sample probe includes:
    at least two sampling probes each having the same length as said reference probe; and
    means for splitting and combining optical signals from said sampling probes.

4. The apparatus of claim 2 wherein there are two reference probes and fiber optic splitter means provides for selected levels of radiation in said reference probes.

5. The apparatus of claim 1 wherein a plurality of spatially distributed fiber optic probes allow for distributed and sequential measurements of optical properties at different locations in the sample.

6. The apparatus of claim 1 wherein a plurality of spatially distributed fiber optic probes allow for simultaneous measurement of optical properties at different locations in the sample.

7. A method for determining the size for particles of a known concentration in a stream of colloidal or particulate suspension comprising the steps of:
    illuminating both a sample of the stream and a reference with a common level of low-coherent electromagnetic radiation;
    combining resultant reflected radiation from said sample and said reference to provide an interference signal;
    determining photon pathlength distribution of said sample; and
    obtaining the particle size from the interference signal using a fitting procedure to obtain the scattering and absorption coefficients.

8. The method of claim 7 wherein the radiation is provided by:
    a plurality of low-coherence sources each having different central wavelengths; and
    a plurality of sample probes and a tunable filter positioned prior to said sample probes.

9. The method of claim 8 wherein there are two reference probes and fiber optic splitter means provides for selected levels of radiation in said reference probes.

10. A method for monitoring and control of an optical property comprising the steps of:
    illuminating both a sample of the stream and a reference with a common level of low-coherent electromagnetic radiation;
    combining resultant reflected radiation from said sample and said reference to provide an interference signal and,
    determining photon pathlength distribution of said sample from the interference signal and a processor responsive to the pathlength distribution and a processor device that compares the measured signal with a prescribed signal; and
    an output device to update an estimation signal as compared with the comparison signal.

11. The method of claim 10 wherein the radiation is provided by:
    a plurality of low-coherence sources each having different central wavelengths; and
    a plurality of sample probes and a tunable filter positioned prior to said sample probes.

12. The method of claim 11 wherein there are two reference probes and fiber optic splitter means provides for selected levels of radiation in said reference probes.

13. A process control apparatus useful comprising;
    a reference probe and at least one sample probe positioned in a flow channel for a stream of colloidal or particulate suspensions;
    at least one low-coherence light source;
    means for illuminating the reference probe and sample probe with a split beam of electromagnetic radiation;

means for converting the photon pathlength distribution of an interference signal into particulate size data; and means for modifying the particulate size of said stream.

14. The method of claim 13 wherein the radiation is provided by:
   a plurality of low-coherence sources each having different central wavelengths; and
   a plurality of sample probes and a tunable filter positioned prior to said sample probes.

15. The method of claim 13 wherein the sample probe includes:
   at least two sampling probes each having the same length as said reference probe; and
   means for splitting and combining optical signals from said sampling probes.

16. The method of claim 15 wherein there are two reference probes and fiber optic splitter means provides for selected levels of radiation in said reference probes.

17. The method of claim 16 wherein there are two reference probes and fiber optic splitter means provides for selected levels of radiation in said reference probes.

18. A particle sizing apparatus comprising:
   a reference probe and at least one sample probe positioned in the flow channel for a stream of colloidal or particulate suspended materials;
   at least one low-coherence light source;
   means for providing a split beam of electromagnetic radiation capable of illuminating a sample probe positioned in said stream and a reference probe;
   means for combining the reflected illuminations from said probes to provide an interference signal;
   particulate density means for converting the photon pathlength distribution of said interference signal into the particulate density of the stream; and,
   means for adjusting the particulate density of the stream.

19. The method of claim 18 wherein the radiation is provided by:
   a plurality of low-coherence sources each having different central wavelengths; and
   a plurality of sample probes and a tunable filter positioned prior to said sample probes.

20. The method of claim 18 wherein the sample probe includes:
   at least two sampling probes each having the same length as said reference probe; and
   means for splitting and combining optical signals from said sampling probes.

* * * * *